United States Patent
Peffly et al.

(10) Patent No.: US 6,248,316 B1
(45) Date of Patent: *Jun. 19, 2001

(54) HAIR STYLING COMPOSITIONS CONTAINING NON-SILICONE AND SILICONE GRAFTED POLYMERS AND LOW LEVEL OF A VOLATILE HYDRATION SOLVENT

(75) Inventors: Marjorie Mossman Peffly, Cincinnati; Peter Marte Torgerson, Washington Court House; Sanjeev Midha, Blue Ash, all of OH (US)

(73) Assignee: The Procter & Gamble Company, Cincinnati, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/887,450

(22) Filed: Jul. 2, 1997

Related U.S. Application Data

(63) Continuation of application No. 08/549,161, filed on Oct. 27, 1995, now abandoned.

(51) Int. Cl.$^7$ ...................................................... A61K 7/11
(52) U.S. Cl. ................................... 424/70.12; 424/70.16; 424/70.17
(58) Field of Search .............................. 424/70.12, 70.16, 424/70.17

(56) References Cited

U.S. PATENT DOCUMENTS

| | | | |
|---|---|---|---|
| 4,954,336 | * | 9/1990 | Chuang et al. ........................ 424/71 |
| 5,019,377 | * | 5/1991 | Torgerson .............................. 424/70 |
| 5,061,481 | * | 10/1991 | Suzuki et al. .......................... 424/63 |
| 5,106,609 | * | 4/1992 | Bolich, Jr. et al. .................... 424/70 |
| 5,166,276 | * | 11/1992 | Hayama et al. ................... 525/329.7 |
| 5,286,477 | * | 2/1994 | Bhatt et al. ............................. 424/47 |
| 5,362,485 | * | 11/1994 | Hayama et al. ....................... 424/70 |
| 5,565,193 | * | 10/1996 | Midha et al. ..................... 424/70.12 |

* cited by examiner

*Primary Examiner*—Margaret G. Moore
(74) *Attorney, Agent, or Firm*—Andrew A Paul; Joan B. Tucker; Stephen T. Murphy

(57) ABSTRACT

A hair styling composition comprising: (a) from about 0.1% to about 15%, by weight, of an adhesive polymer, said polymer being characterized by an organic polymeric backbone wherein said polymer is substantially free of silicone; (b) from about 0.1% to about 15%, by weight, of a silicone grafted adhesive polymer, said polymer being characterized by an organic polymeric backbone, compatible with said adhesive polymer of (a) wherein said silicone grafted adhesive polymer has silicone macromers grafted to said backbone and wherein the number average molecular weight of said silicone macromers is greater than about 500; (c) from about 0.1% to about 15%, by weight, of a hydrocarbon solvent selected from the group consisting of $C_{10}$–$C_{14}$ branched chain hydrocarbons, and mixtures thereof having a boiling point of from about 105° C. to about 260° C.; (d) a polar solvent phase comprising from about 80% to about 99%, by weight of the composition, of a polar solvent selected from the group consisting of water and $C_2$–$C_3$ monohydric alcohols, and mixtures thereof, wherein said composition contains no more than about 15%, by weight, of $C_3$ monohydric alcohol; wherein said organic polymer backbone is soluble in said polar solvent phase, and said silicone macromers of said hair setting polymer are soluble in said hydrocarbon solvent.

20 Claims, No Drawings

HAIR STYLING COMPOSITIONS CONTAINING NON-SILICONE AND SILICONE GRAFTED POLYMERS AND LOW LEVEL OF A VOLATILE HYDRATION SOLVENT

This is a continuation of application Ser. No. 08/549,161, filed on Oct. 27, 1995, now abandoned.

TECHNICAL FIELD

The present invention relates to hair styling compositions containing both silicone and non-silicone organic polymers as a hair setting agents. More particularly, the present invention relates to hairs styling compositions containing these polymers which are solubilized in a hydrocarbon solvent.

BACKGROUND OF THE INVENTION

The desire to have the hair retain a particular shape is widely held. The most common methodology for accomplishing this is the application of a composition to dampened hair, after shampooing and/or conditioning, or to dry, styled hair. These compositions provide temporary setting benefits and they can be removed by water or by shampooing. The materials used in the compositions to provide the setting benefits have generally been resins and have been applied in the form of mousses, gels, lotions or sprays.

Many people desire a high level of style retention, or hold, from a hair spray composition. In typical hair sprays, hold is achieved by the use of resins, such as AMPHOMER$^R$, supplied by National Starch and Chemical Company, and GANTREZ$^R$ SP 225, supplied by GAF. In general, as hair hold for hair spray compositions is increased, the tactile feel of the hair becomes stiffer and hence, less desirable. It is desirable to provide hair spray products which could provide an improved combination of hair hold and hair feel characteristics.

Hair sprays have been conventionally formulated with high amounts of monohydric alcohol solvents, such as ethanol and isopropanol, and relatively low amounts of water since the presence of water adversely affects spray quality. However, it is now particularly desirable to formulate hair spray compositions with reduced levels of volatile organic compounds, such as ethanol, isopropanol, and other volatile materials, such as aerosol propellants. One way to do this is to increase the levels of water in the formulations. In doing so, it would be highly desirable to provide reformulated products which overcome the problems conventionally associated with the addition of water to hair spray products. In particular, higher levels of water can negatively impact hair feel.

Recently, it has become known to utilize silicone grafted organic backbone polymers as hair setting agents in hair-spray compositions and other hair styling compositions, e.g. hair tonics, lotions, rinses, mousses, etc. Silicone grafted polymers can be used to make hair spray compositions which provide hair setting ability with improved hair feel, e.g., increased softness relative to conventional polymeric hair setting agents.

However, it remains desirable to improve the hair feel performance these silicone grafted polymers can provide at a particular level of hair hold, or conversely, to improve hair hold (after application and drying of such compositions) for a particular level of hair feel performance. It is an object of this invention to provide hair spray compositions, and other aqueous, alcohol, or hydroalcoholic-based hair setting solutions, containing both non-silicone as well as silicone grafted organic backbone polymeric hair setting agents that provide such improved combinations of hair feel/hair hold performance.

It is a further object of this invention to provide hair setting compositions, as described above, that provide both improved hair feel and improved hair hold ability for a particular level of silicone grafted polymer in the composition.

It is yet a further object of this invention to provide compositions that meet the above objects for conventional volatile organic solvent level (conventional VOC) compositions, which typically contain greater than 80% of volatile organic compounds, as well as for reduced volatile organic solvent level (reduced VOC) compositions, i.e., compositions having 80% or less volatile organic solvents.

These and other benefits as may be apparent from the description below can be obtained by the present invention.

The present compositions can comprise, consist of, or consist essentially of any of the required or optional ingredients and/or limitations described herein.

All percentages and ratios are calculated on a weight basis unless otherwise indicated. All percentages are calculated based upon the total composition unless otherwise indicated.

All ingredient levels are refer to the active level of that ingredient, and are exclusive of solvents, by-products, or other impurities that may be present in commercially available sources, unless otherwise indicated.

SUMMARY OF THE INVENTION

The present invention relates to hair styling compositions comprising:

(a) from about 0.1% to about 15%, by weight, of an adhesive polymer having a weight average molecular weight of greater than about 20,000, said polymer being characterized by an organic polymeric backbone wherein said polymer is substantially free of silicone;

(b) from about 0.1% to about 15%, by weight, of a silicone grafted adhesive polymer, said polymer being characterized by an organic polymeric backbone, compatible with said adhesive polymer of (a) wherein said silicone grafted adhesive polymer has silicone macromers grafted to said backbone and wherein the number average molecular weight of said silicone macromers is greater than about 500;

(c) from about 0.1% to about 15%, by weight, of a hydrocarbon solvent selected from the group consisting of $C_{10}$–$C_{14}$ branched chain hydrocarbons, and mixtures thereof having a boiling point of from about 105° C. to about 260° C.;

(d) a polar solvent phase comprising from about 80% to about 99%, by weight of the composition, of a polar solvent selected from the group consisting of water and $C_2$–$C_3$ monohydric alcohols, and mixtures thereof, wherein said composition contains no more than about 15%, by weight, of $C_3$ monohydric alcohol;

wherein said organic polymer backbones of (a) and (b) are soluble in said polar solvent phase, and said silicone macromers of said hair setting polymer are soluble in said hydrocarbon solvent.

By "substantially free" is meant that the polymer contains less than about 0.5%, preferably less than about 0.1%, more preferably less than about 0.05% silicone.

In preferred embodiments, the compositions hereof additionally comprise a plasticizer for the silicone grafted hair setting polymer. Especially preferred plasticizers include di-isobutyl adepate and acetyl tri-$C_2$–$C_8$ alkyl citrates, particularly acetyl triethyl citrate.

DETAILED DESCRIPTION OF THE INVENTION

The essential components of the present invention are described below. Also included is a nonexclusive description of various optional and preferred components useful in embodiments of the present invention.

Adhesive Polymer

The compositions of the present invention essentially comprise an adhesive polymer as a hair setting agent. The compositions hereof will generally comprise from about 0.1% to about 15%, preferably from 0.5% to about 8%, more preferably from about 1% to about 8%, by weight of the composition, of the adhesive polymer. It is not intended to exclude the use of higher or lower levels of the polymers, as long as an effective amount is used to provide adhesive or film-forming properties to the composition and the composition can be formulated and effectively applied for its intended purpose. By adhesive polymer what is meant is that when applied as a solution to a surface and dried, the polymer forms a film. Such a film will have adhesive and cohesive strength, as is understood by those skilled in the art.

The adhesive polymer will preferably be a carbon chain derived from polymerization of ethylenically unsaturated monomers, but can also be, cellulosic chains or other carbohydrate-derived polymeric chains. The backbone can also include ether groups, ester groups, amide groups urethanes and the like.

The adhesive polymer should have a weight average molecular weight of at least about 20,000, preferably greater than about 25,000, more preferably greater than about 30,000, most preferably greater than about 35,000. There is no upper limit for molecular weight except that which limits applicability of the invention for practical reasons, such as processing, aesthetic characteristics, formulateability, etc. In general, the weight average molecular weight will be less than about 10,000,000, more generally less than about 5,000,000, and typically less than about 2,000,000. Preferably, the weight average molecular weight will be between about 20,000 and about 2,000,000, more preferably between about 30,000 and about 1,000,000, and most preferably between about 40,000 and about 500,000.

Preferably, the adhesive hereof when dried to form a film have a Tg or Tm of at least about −20° C., more preferably at least about 20° C., so that they are not unduly sticky, or "tacky" to the touch. As used herein, the abbreviation "Tg" refers to the glass transition temperature of the backbone of the polymer, and the abbreviation "Tm" refers to the crystalline melting point of the backbone, if such a transition exists for a given polymer. Preferably, both the Tg and the Tm, if any, are above about −20° C., more preferably above about 20° C.

The adhesive polymer monomer units can be derived from polar, or hydrophilic, monomers, "A" monomers, low polarity, or hydrophobic, "B" monomers, or mixtures of polar hydrophilic "A" monomers and low polarity, hydrophobic, "B" monomers. The silicone grafted polymer preferably comprises from about 1% to about 99%, by weight, of hydrophilic monomer units and about 0% to about 99%, by weight, of hydrophobic monomer units.

Hydrophobic monomers means monomers which form substantially water insoluble homopolymers. Hydrophilic monomers means monomers which form homopolymers which are substantially water soluble. Substantially water soluble shall refer to monomers that form homopolymers that are soluble in distilled (or equivalent) water, at 25° C., at a concentration of 0.2% by weight, and are preferably soluble at 1.0% by weight. Substantially water insoluble shall refer to monomers that form homopolymers that are not soluble in distilled (or equivalent) water, at 25° C., at a concentration of 0.2% by weight, and preferably not soluble at 0.1% by weight. The weight average molecular weight for purposes of determining substantial water solubility or insolubility shall be about 40,000, although solubility at higher molecular weight shall also be indicative of solubility at about 40,000.

The particular relative amounts of A and B monomers can vary as long as the polymer is soluble in the polar solvent hereof.

Representative examples of A monomers include acrylic acid, methacrylic acid, N,N-dimethylacrylamide, dimethyl aminoethyl methacrylate, quaternized dimethylaminoethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, diallyidimethyl ammonium chloride, vinyl pyrrolidone, vinyl ethers (such as methyl vinyl ether), maleimides, vinyl pyridine, vinyl imidazole, other polar vinyl heterocyclics, styrene sulfonate, allyl alcohol, vinyl alcohol (such as that produced by the hydrolysis of vinyl acetate after polymerization), salts of any acids and amines listed above, and mixtures thereof. Preferred A monomers include acrylic acid, N,N-dimethyl acrylamide, dimethylaminoethyl methacrylate, quaternized dimethyl aminoethyl methacrylate, vinyl pyrrolidone, salts of acids and amines listed above, and mixtures thereof.

Representative examples of B monomers are acrylic or methacrylic acid esters of $C_1$–$C_{18}$ alcohols, such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol(2-methyl-2-propanol), cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-tri methyl-1-hexanol, 1-decanol, 1-dodecanol, 1-hexadecanol, 1-octa decanol, and the like, the alcohols having from about 1–18 carbon atoms with the number of carbon atoms preferably being from about 1–12; styrene; polystyrene macromer; vinyl acetate; vinyl chloride; vinylidene chloride; vinyl propionate; alpha-methylstyrene; t-butylstyrene; butadiene; cyclohexadiene; ethylene; propylene; vinyl toluene; and mixtures thereof. Preferred B monomers include n-butyl methacrylate, isobutyl methacrylate, t-butyl acrylate, t-butyl methacrylate, 2-ethylhexyl methacrylate, methyl methacrylate, and mixtures thereof. Most preferably, B is selected from t-butyl acrylate, t-butyl methacrylate, and mixtures thereof.

The level of A monomer units can be from about 0% to about 100%, preferably from about 5% to about 80%, more preferably from about 10% to about 50%, most preferably from about 15% to about 40%; the level of B monomer units, can be from 0% to about 100%, preferably from about 20% to about 95%, more preferably from about 50% to about 90%, most preferably from about 60% to about 85%.

The composition of any particular adhesive polymer will help determine its formulational properties. By appropriate selection and combination of particular A and B components, the adhesive polymer can be optimized for inclusion in specific vehicles. The adhesive polymer included in the compositions hereof must be soluble in the polar solvent. This is determined according to whether the polymer can stay in solution or precipitates out of solution at 25° C. at the concentration present in the composition. It is well within the skill of one in the art to select monomers for incorporation into the polymers for formulateability and solubility in selected polar solvent systems.

Exemplary adhesive polymers for use in the present invention include the following, where the numbers following the structure indicate the weight ratios of monomers as loaded into the polymerization reactor (i) acrylic acid/t-butyl acrylate 25/75
(ii) dimethylaminoethyl methacrylate/isobutyl methacrylate/2-ethylhexyl-methacrylate 40/40/20
(iii) t-butylacrylate/acrylic acid 65/35
(iv) polymer (ii) quaternized by treatment with methyl choride The adhesive polymers can be synthesized by free radical polymerization of the monomers. The general principles of free radical polymerization methods are well understood. See, for example, Odian, "Principles of Polymerization", 3nd edition, John Wiley & Sons, 1991, pp. 198–334. The desired monomers are all placed in a reactor, along with a sufficient amount of a mutual solvent so that when the reaction is complete the viscosity of the reaction is reasonable. Typical monomer loadings are from about 20% to about 50%. Undesired terminators, especially oxygen, are removed as needed. This is done by evacuation or by purging with an inert gas, such as argon or nitrogen. The initiator is introduced and the reaction brought to the temperature needed for initiation to occur, assuming thermal initiators are used. Alternatively, redox or radiation initiation can be used. The polymerization is allowed to proceed as long as needed for a high level of conversion to be achieved, typically from a few hours to a few days. The solvent is then removed, usually by evaporation or by precipitating the polymer by addition of a nonsolvent. The polymer can be further purified, as desired.

As an alternative to a batch reaction, the adhesive polymer can be made by a semi-continuous or continuous process. In the semi-continuous process, two or more additions of monomers are made during the polymerization reaction. This is advantageous when the polymer is made of several monomers which react during the polymerization at different rates. The proportions of monomers added to the reaction at the separate points of addition can be adjusted by one of ordinary skill in the art such that the polymers of the final product have a more uniform structure. In other words, the polymers of the final product will have a more consistent monomer content distribution for each of the monomer types charged to the reaction.

As is known in the art, polymers which have acidic functionalities, such as carboxyl groups, are usually used in at least partially neutralized form to promote solubility/dispersibility of the polymer. In addition, use of the neutralized form aids in the ability of the hair care compositions to be removed from the hair by shampooing. In general, it is preferred that from about 10% to 100%, more preferably from about 20% to about 90%, and most more preferably from about 40% to about 85%, of the acidic monomers of the polymer be neutralized.

Any conventionally used base, organic or metallic, may be used for neutralization of the polymers. Metallic bases are particularly useful in the present compositions. Hydroxides, where the cation is an alkali metal or an alkaline earth metal, are suitable neutralizers for use in the present hair spray compositions.

Preferred neutralizing agents for use in hair spray compositions of the present invention are potassium hydroxide and sodium hydroxide.

Examples of other suitable neutralizing agents which may be included in the hair spray compositions of the present invention include amines, especially amino alcohols such as 2-amino-2-methyl-1,3-propanediol (AMPD), 2-amine-2-ethyl-1,3-propanediol (AEPD), 2-amino-2-methyl-1-propanol (AMP), 2-amino-1-butanol (AB), monoethanolamine (MEA), diethanolamine (DEA), triethanolamine (TEA), monoisopropanolamine (MIPA), diisopropanolamine (DIPA), tri-isopropanolamine (TIPA) and dimethyl steramine (DMS). Particularly useful neutralizing agents are mixtures of amines and metallic bases.

Polymers having basic functionalities, e.g., amino groups, are preferably at least partially neutralized with an acid, e.g., hydrogen chloride.

Solubility of the adhesive polymer, as described above, should be determined after neutralization, if any, as well as after addition of other ingredients that may be included in the polar solvent phase, such as surfactants, solubilizers, etc.

Silicone Grafted Adhesive Polymer

In addition to the adhesive hair styling polymer the compositions according to the invention comprise, as a second essential component, a silicone-containing hair styling resin which is compatible with the adhesive polymer described above. This silicone containing hair styling resin is preferably colloidally dispersed or solubilized in the hair cosmetic carrier along with the adhesive hair styling polymer. Keeping the two hair styling agents dispersed and solubilised in the hair spray solvent is believed to be important for providing the unique hair setting benefits in combination with excellent hair feel characteristics which are delivered by compositions according to the present invention.

The compositions hereof will generally comprise from about 0.1% to about 15%, preferably from 0.5% to about 8%, more preferably from about 1% to about 8%, by weight of the composition, of the silicone grafted polymer. It is not intended to exclude the use of higher or lower levels of the polymers, as long as an effective amount is used to provide adhesive or film-forming properties to the composition and the composition can be formulated and effectively applied for its intended purpose. By adhesive polymer what is meant is that when applied as a solution to a surface and dried, the polymer forms a film. Such a film will have adhesive and cohesive strength, as is understood by those skilled in the art.

The silicone grafted polymers are characterized by polysiloxane moieties covalently bonded to and pendant from a polymeric carbon-based backbone. The polymeric backbone is chosen such that it is compatible with the non-silicone adhesive styling polymer. By "compatible" is meant is that, when placed in a suitable solvent, the polymers form a stable solution, i. e., the polymers do not compete for solubility and therefore, cause no phase separation and when the solution is dried a uniform film is formed, with no macrophase separation of the two polymers. A suitable solvent is a solvent which substantially completely dissolves the non-silicone and silicone grafted polymers at the levels described herein. The polymer blend forms a relatively clear hairspray system (% transmittance at 450 nm is generally greater than 80%). It is recognized that certain plasticizers can form cloudy films as well as incorrect neutralization levels. Therefore, this would fall outside this definition of compatibility. The compatibility can be tested by dissolving the adhesive polymer and the silicone grafted hair styling resin in a mutual solvent, and then evaporating the solvent to form a film. Incompatible polymers will form a cloudy film with poor mechanical properties, due to the large scale phase separation of the two polymers. Alternatively, after drying the polymer solution to a film, compatibility can be evaluated by measuring the Tg. Compatible polymers will have a single Tg, while incompatible polymers will exhibit two Tg's. Although compatibility can occur between two polymers of completely different structures, it is preferred that compatibility be obtained by making the composition of the non-silicone backbone of the silicone grafted polymer similar to or identical to the composition of the adhesive polymer.

The backbone will preferably be a carbon chain derived from polymerization of ethylenically unsaturated monomers, but can also be cellulosic chains or other carbohydrate-derived polymeric chains to which polysiloxane moieties are pendant. The backbone can also include ether groups, ester groups, amide groups, urethane groups and the like. The polysiloxane moieties can be substituted on the polymer or can be made by co-polymerization of polysiloxane-containing polymerizable monomers (e.g. ethylenically unsaturated monomers, ethers, and/or epoxides) with non-polysiloxane-containing polymerizable monomers.

The polysiloxane-grafted polymer should have a weight average molecular weight of at least about 20,000. There is no upper limit for molecular weight except that which limits applicability of the invention for practical reasons, such as processing, aesthetic characteristics, formulateability, etc. In general, the weight average molecular weight will be less than about 10,000,000, more generally less than about 5,000,000, and typically less than about 3,000,000. Preferably, the weight average molecular weight will be between about 50,000 and about 2,000,000, more preferably between about 75,000 and about 1,000,000, most preferably between about 100,000 and about 750,000.

Preferably, the adhesive hereof when dried to form a film have a Tg or Tm of at least about −20° C., more preferably at least about 20° C., so that they are not unduly sticky, or "tacky" to the touch. As used herein, the abbreviation "Tg" refers to the glass transition temperature of the backbone of the polymer, and the abbreviation "Tm" refers to the crystalline melting point of the backbone, if such a transition exists for a given polymer. Preferably, both the Tg and the Tm, if any, are above about −20° C., more preferably above about 20° C.

The silicone grafted polymers for the compositions of the present invention comprise "silicone-containing" (or "polysiloxane-containing") monomers, which form the silicone macromer pendant from the backbone, and non-silicone-containing monomers, which form the organic backbone of the polymer.

The silicone grafted polymers should satisfy the following three criteria:
 (1) when dried, either alone or in the presence of the adhesive polymer, the polymer phase-separates into a discontinuous phase which includes the polysiloxane portion and a continuous phase which includes the non-polysiloxane portion;
 (2) the polysiloxane portion is covalently bonded to the non-polysiloxane portion; and
 (3) the molecular weight of the polysiloxane portion is at least about 500.

When used in a composition, such as a personal care composition for application to the hair or skin, the non-polysiloxane portion should permit the polymer to deposit on the intended surface, such as hair or skin.

Without being limited by theory, it is believed that the phase separation property provides a specific orientation of the polymer which results in the desired combination of tactile feel, and film-forming or adhesive benefits. The phase-separating nature of the compositions of the present invention may be determined as follows:

The polymer is cast as a solid film out of a solvent (i.e., a solvent which dissolves both the backbone and the polysiloxane-graft portions). This film is then sectioned and examined by transmission electron microscopy. Microphase separation is demonstrated by the observation of inclusions in the continuous phase. These inclusions should have the proper size to match the size of the silicone chain (typically a few hundred nm or less) and the proper density to match the amount of silicone present. This behavior is well documented in the literature for polymers with this structure (see, for example, S. D. Smith, Ph.D. Thesis, University of Virginia, 1987, and references cited therein, said thesis incorporated by reference herein).

A second method for determining phase-separating characteristics involves examining the enrichment of the concentration of silicone at the surface of a polymer film relative to the concentration in the bulk polymer. Since the silicone prefers the low energy air interface, it preferentially orients on the polymer surface. This produces a surface with the silicone oriented at the surface of the film. This can be demonstrated experimentally by ESCA (electron spectroscopy for chemical analysis) of the dried film surface. Such an analysis shows a high level of silicone and a greatly reduced level of backbone polymer when the film surface is analyzed. (Surface here means the first few tens of Angstroms of film thickness.) By varying the angle of the interrogating beam the surface can be analyzed to varying depths.

The preferred silicone grafted polymers comprise an organic backbone preferably a carbon backbone derived from ethylenically unsaturated monomers, such as a vinyl polymeric backbone, and a polysiloxane macromer (especially preferred are polydialkylsiloxane, most preferably polydimethylsiloxane) grafted to the backbone. The polysiloxane macromer should have a weight average molecular weight of at least about 500, preferably from about 1,000 to about 100,000, more preferably from about 2,000 to about 50,000, most preferably about 5,000 to about 20,000. Organic backbones contemplated include those that are derived from polymerizable, ethylenically unsaturated monomers, including vinyl monomers, and other condensation monomers (e.g., those that polymerize to form polyamides and polyesters), ring-opening monomers (e.g., ethyl oxazoline and caprolactone), etc. Also contemplated are backbones based on cellulosic chains, ether-containing backbones, etc.

Preferably the weight ratio of the non-silicone polymer to silicone grafted polymer ranges from about 1:10 to about 1:1, preferably from about 1:5 to about 1:1.

Examples of useful polymers and how they are made are described in detail in U.S. Pat. No. 4,693,935, Mazurek, issued Sep. 15, 1987, U.S. Pat. No. 4,728,571, Clemens et al., issued Mar. 1, 1988, both of which are incorporated herein by reference.

Suitable silicone grafted polymers are also disclosed in EPO Application 90307528.1, published as EPO Application 0 408 311 A2 on Jan. 11, 1991, Hayama, et al., U.S. Pat. No. 5,061,481, issued Oct. 29, 1991, Suzuki et al., U.S. Pat. No. 5,106,609, Bolich et al., issued Apr. 21, 1992, U.S. Pat.

No. 5,100,658, Bolich et al., issued Mar. 31, 1992, U.S. Pat. No. 5,100,657, Ansher-Jackson, et al., issued Mar. 31, 1992, U.S. Pat. No. 5,104,646, Bolich et al., issued Apr. 14, 1992, U.S. Ser. No. 07/758,319, Bolich et al, filed Aug. 27, 1991, now abandoned and U.S. Ser. No. 07/758,320, Torgerson et al., filed Aug. 27, 1991, now abandoned, all of which are incorporated by reference herein.

The preferred silicone grafted polymers are comprised of monomer units derived from: at least one free radically polymerizable ethylenically unsaturated monomer or monomers and at least one free radically polymerizable polysiloxane-containing ethylenically unsaturated monomer or monomers.

The silicone grafted polymers hereof generally comprise from about 1% to about 50%, by weight, of polysiloxane-containing monomer units, i.e., monomer units polysiloxane-containing monomers (referred to herein as "C" monomers), and from about 50% to about 99% by weight, of non-polysiloxane-containing monomers.

The non-polysiloxane-containing monomer units can be derived from polar, or hydrophilic, monomers, "A" monomers, or mixtures of polar hydrophilic monomers, low polarity, or hydrophobic, "B" monomers or mixtures of the two. The definitions of the "A" and "B" monomers, and representative examples of the "A" and "B" monomers, are the same as those use for the "A" and "B" monomers in the adhesive polymer.

The particular relative amounts of A, B, and C monomers can vary as long as the polymer backbone is soluble in the polar solvent hereof, the polymer backbone is compatible with the adhesive polymer, and the silicone grafted copolymer exhibits phase separation when dried.

Polymerizable polysiloxane-containing monomers (C monomer) are exemplified by the general formula:

$$X(Y)_n Si(R)_{3-m} Z_m$$

wherein X is an ethylenically unsaturated group copolymerizable with the A and B monomers, such as a vinyl group; Y is a divalent linking group; R is a hydrogen, hydroxyl, lower alkyl (e.g. $C_1$–$C_4$), aryl, alkaryl, alkoxy, or alkylamino; Z is a monovalent siloxane polymeric moiety having a number average molecular weight of at least about 500, is essentially unreactive under copolymerization conditions, and is pendant from the vinyl polymeric backbone described above; n is 0 or 1; and m is an integer from 1 to 3. C has a weight average molecular weight as described above. Preferably, the C monomer has a formula selected from the following group:

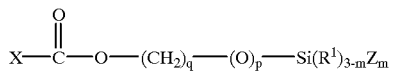

In this structure, m is 1, 2 or 3 (preferably m=1); p is 0 or 1; q is an integer from 2 to 6; $R^1$ is hydrogen, hydroxyl, lower alkyl, alkoxy, alkylamino, aryl, or alkaryl (preferably $R^1$ is alkyl); X is

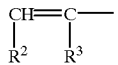

$R^2$ is hydrogen or —COOH (preferably $R^2$ is hydrogen); $R^3$ is hydrogen, methyl or —$CH_2COOH$ (preferably $R^3$ is methyl); Z is

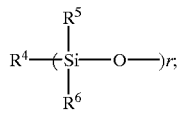

$R^4$, $R^5$, and $R^6$ independently are lower alkyl, alkoxy, alkylamino, aryl, arkaryl, hydrogen or hydroxyl (preferably $R^4$, $R^5$, and $R^6$ are alkyls); and r is an integer of about 5 or higher, preferably about 10 to about 1500 (most preferably r is from about 100 to about 250). Most preferably, $R^4$, $R^5$, and $R^6$ are methyl, p=0, and q=3. Also preferred, the C monomer has the formula selected from the group:

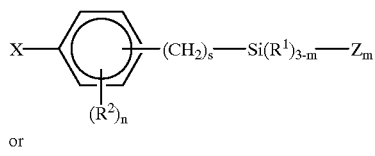

or

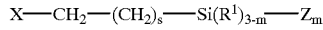

wherein: s is an integer from 0 to about 6, preferably 0, 1, or 2, more preferably 0 or 1; m is an integer from 1 to 3, preferably 1; $R^2$ is C1–C10 alkyl or C7–C10 alkylaryl, preferably C1–C6 alkyl or C7–C10 alkylaryl, more preferably $C_1$–$C_2$ alkyl; n is an integer from 0 to 4, preferably 0 or 1, more preferably 0.

In general, the silicone grafted polymer will preferably comprise from about 50% to about 99%, more preferably from about 60% to about 98%, most preferably from about 75% to about 95%, by weight of the polymer, of non-silicone macromer-containing monomer units, e.g. the total A and B monomer units, and from about 1% to about 50%, preferably from about 2% to about 40%, more preferably from about 5% to about 25%, of silicone macromer-containing monomer units, e.g. the C monomer units. The level of A monomer units can be from about 0% to about 99%, preferably from about 5% to about 80%, more preferably from about 10% to about 50%, most preferably from about 15% to about 40%; the level of B monomer units, can be from about 0% to about 99%, preferably from about 1% to about 90%, more preferably from about 5% to about 85%, most preferably from about 15% to about 80%; and the level of C monomer units, from about 1% to about 50%, preferably from about 2% to about 40%, more preferably from about 5% to about 25%.

The combination of the A and B monomers preferably comprises from about 50.0% to about 99.9% (more preferably about 60% to about 99%, most preferably from about 75% to about 95%) of the polymer. The composition of any particular copolymer will help determine its formulational properties. In fact, by appropriate selection and combination of particular A, B and C components, the copolymer can be optimized for inclusion in specific vehicles. For example, polymers which are soluble in an aqueous formulation preferably have the composition: from about 0% to about 70% (preferably from about 5% to about 70%) monomer A, from about 30% to about 98% (preferably from about 30% to about 80%) monomer B, and from about 1% to about 40% monomer C. Polymers which are dispersible have the preferred composition: from about 0% to about 70% (more preferably from about 5% to about 70%) monomer A, from about 20% to about 80% (more preferably from about 20% to about 60%) monomer B, and from about 1% to about 40% monomer C.

The composition of any particular silicone grafted polymer will help determine its formulational properties. By appropriate selection and combination of particular A, B and C components, the silicone grafted polymer can be optimized for inclusion in specific vehicles. The backbone of the silicone grafted polymer included in the compositions hereof must be soluble in the polar solvent, which is hereinafter referred to as the silicone grafted polymer, as a whole, being soluble in the polar solvent. This is determined according to whether the polymer can stay in solution or precipitates out of solution at 25° C. at the concentration present in the composition or whether the range of concentrations for silicone grafted polymer discribed herein. It is well within the skill of one in the art to select monomers for incorporation into the polymers for formulateability and solubility in selected polar solvent systems.

Exemplary silicone grafted polymers for use in the present invention include the following, where the composition is given as weight part of monomer used in the synthesis:
  (i) acrylic acid/n-butylmethacrylate/polydimethylsiloxane (PDMS) macromer 20,000 molecular weight macromer 20(70/10
  (ii) dimethylaminoethyl methacrylate/isobutyl methacrylate/2-ethylhexyl-methacrylate/PDMS macromer-20,000 molecular weight macromer 40/30/15/15
  (iii) t-butylacrylate/acrylic acid/PDMS macromer-10,000 molecular weight macromer 63.5/20/16.5
  (iv) t-butylacrylate/acrylic acid/PDMS macromer-20,000 molecular weight macromer 60/20/20

The silicone grafted polymers can be synthesized by free radical polymerization of the polysiloxane-containing monomers with the non-polysiloxane-containing monomers. The synthetic procedures are in general the same as those described for the adhesive copolymer. The silicone macromer is added in to the reactor along with the "A" and "B" monomers, and the reaction proceeds as for the adhesive copolymer examples. Compared to the adhesive copoymer, it may be necessary to choose different solvents for the polymerization reaction, as apparent to one skilled in the art, to keep the monomers and polymers in solution thrroughout the polymerization.

Without being limited by theory, it is believed that in forming the above-described silicone grafted polymers, there is some polymer which does not encorporate the silicone graft; such polymers have a relatively low weight average molecular weight e.g., below 20,000.

Polar Solvent Phase

The liquid care compositions of the present invention also include a polar solvent phase as a liquid vehicle for the silicone grafted polymer. The polar solvent phases comprise one or more polar solvents that are present in the hair care compositions at a level of from about 80% to about 99%, preferably from about 85% to about 98%, more preferably from about 90% to about 95% of the total composition.

The polar solvents essential to the present compositions are selected from the group consisting of water, $C_2$–$C_3$ monohydric alkanols, and mixtures thereof. If present, $C_3$ alkanols, such as isopropanol, should be used at levels no greater than about 15% by weight of the composition, preferably no greater than about 12%, more preferably no greater than about 10%. High levels of $C_3$ monohydric alcohols are undesirable in the present compositions due to potential odor issues they can create. Preferred polar solvent phases contain water, ethanol, or mixtures thereof. Preferably the organic polymer backbones of the adhesive polymer and the silicone grafted polymer are insoluble in said polar solvent.

Where water and alcohol mixtures are used, for instance, water-ethanol or water-isopropanol-ethanol, the water content of the compositions is generally in the range of from about 0.5% to about 99%, preferably from about 5% to about 50% by weight of the total composition. In such mixtures, the alcohol solvents are generally present in the range of from 0.5% to about 99%, preferably from about 50% to about 95%, by weight of the total composition.

In yet another aspect of this invention are provided hair styling products, such as hair spray compositions, which contain reduced levels of volatile organic solvents. A reduced volatile organic solvent hair spray composition of the present invention contains no more than 80% volatile organic solvents (which include, for example, alkanols but not water). As used herein, volatile organic solvents means solvents which have at least one carbon atom and exhibit a vapor pressure of greater than 0.1 mm Hg at 20° C.

In the reduced volatile organic solvent hair styling products hereof, the compositions generally comprise at least 10%, by weight, of water. It is also specifically contemplated that they may contain at least about 11%, 12%, 13%, 14%, 15%, or more water.

The reduced volatile organic solvent compositions hereof will comprise up to about 90%, preferably up to about 70%, more preferably up to about 60% even more preferably no more than about 50%, water; and from about 10% to about 80%, preferably from about 20% to about 80%, more preferably from about 40% to about 80%, of volatile organic solvent. It is also contemplated that the compositions can be limited to containing no more than about 75%, 65%, 55%, or other levels of volatile organic solvents.

Nonpolar, Branched Chain Hydrocarbon

The compositions hereof contain as an essential element a volatile, nonpolar, branched chain hydrocarbon, which acts as a solvent for the silicone portion of the silicone grafted copolymer and is safe for topical application to the skin and hair. The branched chain hydrocarbon solvent hereof is present at a level of from about 0.1% to about 15%, preferably from about 0.5% to about 10%, more preferably from about 2% to about 8%, by weight of the composition.

The branched chain hydrocarbon solvent is characterized by a boiling point of at least about 105° C., preferably at least about 110° C., more preferably at least about 125° C., most preferably at least about 150° C. The boiling point is also generally about 260° C. or less, preferably about 200° C. or less. The hydrocarbon chosen should also be safe for topical application to the hair and skin.

The branched chain hydrocarbon solvents are selected from the group consisting of $C_{10}$–$C_{14}$ branched chain hydrocarbons, and mixtures thereof, preferably $C_{11}$–$C_{13}$ branched chain hydrocarbons, more preferably $C_{12}$ branched chain hydrocarbons. Saturated hydrocarbons are preferred, although it isn't necessarily intended to exclude unsaturated hydrocarbons.

Examples of suitable nonpolar solvents include isoparaffins of the above chain sizes. Isoparaffins are commercially available from Exxon Chemical Co. Examples include Isopar™ G ($C_{10}$–$C_{11}$ isoparaffins), Isopar™ H and K ($C_{11}$–$C_{12}$ isoparaffins), and isopar™ L ($C_{11}$–$C_{13}$ isoparaffins). The most preferred nonpolar solvent are $C_{12}$ branched chain hydrocarbons, especially isododecane. Isododecane is commercially available from Preperse, Inc. (South Plainfield, N.J., USA) as Permethyl™ 99A.

The silicone macromer portion of the silicone grafted polymer is soluble in the nonpolar hydrocarbon solvent in the present compositions. This can be easily determined by verifying whether a silicone macromer of the same composition and molecular weight as that grafted to the silicone grafted polymer is soluble in the nonpolar hydrcarbon solvent. In general, the macromer should be soluble at 25° C. at a concentration of 0.1% by weight of the hydrocarbon solvent, preferably at 1%, more preferably at 5%, most preferably at 15%.

The nonpolar hydrocarbon solvent, however, is insoluble in the polar solvent of the composition. This is determined in the absence of the silicone grafted polymer, or other emulsifying agents, and can easily be verified by observing whether the polar and nonpolar solvents form separate phases after being mixed together.

Without intending to be necessarily limited by any particular theory, it is believed that the nonpolar hydrocarbon solvent solubilizes the silicone macromer portion of the silicone grafted polymer. This is believed to aid in obtaining a smoother polymer film upon drying. Since the hydrocarbon solvent is less volatile than the polar solvent phase, the hydrocarbon solvent maintains the silicone portions in solubilized form for a relatively long period as the composition dries, thus minimizing aggregation of the silicone portions and, therefore, allowing the polymer to dry as a smoother film.

Plasticizer

The compositions hereof can optionally contain a plasticizer for the silicone grafted polymer. Any plasticizer suitable for use in hair care products or for topical application to the hair or skin can be used. A wide variety of plasticizers are known in the art. These include acetyl triethylcitrate, triethycitrate, glycerin, diisobutyl adipate, butyl stearate, and propylene glycol. Plasticizers are typically used at levels of from about 0.01% to about 10%, by weight of the composition, preferably from about 0.05% to about 3%, more preferably from about 0.05% to about 1%.

Optional Ingredients

The present compositions can contain a wide variety of optional ingredients, including among them any of the types of ingredients known in the art for use in hair setting compositions, especially hair spray compositions and hair setting tonics. These ingredients include, but are not limited to, surfactants (including fluorinated surfactants and silicone copolyols), and ionic strength modifiers, propellants, hair conditioning agents (e.g., silicone fluids, fatty esters, fatty alcohols, long chain hydrocarbons, cationic surfactants, etc.)

Ionic Strength Modifier System

Optionally, the compositions of the present invention can contain an effective amount of a non-surface active ionic strength modifier system for reducing the viscosity of the hair spray composition. When used, the ionic strength modifiers will be present in the present compositions at a level of at least about 0.01%, by weight of the composition. The upper limit is dependent upon the maximum amount of the ionic strength modifiers that can be present in the particular compositions hereof such that the hair setting resin remains solubilized or dispersed. As will be understood by those skilled in the art, as the ionic strength of the composition is increased, the resin will eventually fall out of solution, or otherwise no longer remain solubilized or dispersed in the polar liquid carrier. The upper limit of the ionic strength modifier system level will vary depending upon the particular ionic strength modifiers, liquid vehicle, resin, and other ingredients present in the composition. Thus, for example, the maximum amount of the ionic strength modifiers that can be used will tend to be lower for compositions with liquid vehicles containing less water, compared to compositions with more water. Generally, the compositions will comprise about 4%, by weight, or less of the ionic strength modifiers, more generally about 2% or less, and typically about 1% or less. Preferably, the compositions hereof will comprise from about 0.01% to about 0.5%, more preferably from about 0.01% to about 0.1%, of the ionic strength modifier system.

The ionic strength modifier system comprises a mixture of monomeric cations and anions. The ions of the ionic strength modifier system hereof are non-surface active, i.e. they do not significantly reduce surface tension. For purposes hereof, non-surface active shall mean the ions, which at a 0.5% aqueous solution concentration, reduce surface tension by no more than 5.0 dynes/cm2. Generally, the ions of the ionic strength modifier system hereof will be characterized by having, at maximum, four or less carbon atoms per charge, preferably two or less carbon atoms, in any aliphatic chain or straight or branched chain organic heterochain.

The ionic strength modifier system comprises monomeric ions of the type which are products of acid-base reactions. Thus, basic and acidic ions $OH^-$ and $H^+$ do not constitute part of the ionic strength modifier system hereof, although they may be present in the composition. The ions hereof are incorporated into the composition in a form such that they can exist in the composition as free ions, i.e., in dissociated form. It is not necessary that all of the ions added exist in the composition as free ions, but must be at least partially soluble or dissociated in the composition. The ionic strength modifiers can be incorporated into the hair styling compositions, for example, by addition of soluble salts, or by addition of mixtures of acids and bases, or by a combination thereof. It is a necessary aspect of the invention that both anions and cations of the ionic strength modifier system be included in the composition.

Suitable cations for use include, for example, alkali metals, such as lithium, sodium, and potassium, and alkaline-earth metals, such as magnesium, calcium, and strontium. Preferred of the divalent cations is magnesium. Preferred monovalent metal ions are lithium, sodium, and potassium, particularly sodium and potassium. Suitable means of addition to the compositions hereof include, for example, addition as bases, e.g., hydroxides, sodium hydroxide and potassium hydroxide, and such as salts that are soluble in the liquid carrier, e.g. salts of monomeric anions such as those described below.

Other suitable cations include organic ions, such as quaternary ammonium ions and cationic amines, such as ammonium mono-, di-, and tri-ethanolamines, triethylamine, morpholine, aminomethylpropanol (AMP), aminoethylpropanediol, etc. Ammonium and the amines are preferably provided in the forms of salts, such as hydrochloride salts.

Monomeric anions that can be used include halogen ions, such as chloride, fluoride, bromide, and iodide, particularly chloride, sulfate, ethyl sulfate, methyl sulfate, cyclohexyl sulfamate, thiosulfate, toluene sulfonate, xylene sulfonate, citrate, nitrate, bicarbonate, adipate, succinate, saccharinate, benzoate, lactate, borate, isethionate, tartrate, and other monomeric anions that can exist in dissociated form in the hair styling composition. The anions can be added to the compositions hereof, for example, in the form of acids or salts which are at least partially soluble in the liquid vehicle, e.g., sodium or potassium salts of acetate, citrate, nitrate, chloride, sulfate, etc. Preferably, such salts are entirely soluble in the vehicle.

The use of ionic strength modifiers are especially useful in reduced volatile organic solvent compositions, most especially those utilizing silicone macromer-containing polymers.

Hair Styling Compositions

The present invention encompasses a wide variety of hair styling compositions, including hair spray compositions, mousses, and hair setting tonics. In general, the compositions will be flowable, low viscosity compositions that, preferably, are suitable for spray application. Higher viscosity compositions are also contemplated, however.

Hair spray compositions and mousses of the present invention can be dispensed from containers which are aerosol dispensers or pump spray dispensers. Such dispensers, i.e., containers, are well known to those skilled in the art and are commercially available from a variety of manufacturers, including American National Can Corp. and Continental Can Corp.

When the hair spray compositions are to be dispensed from a pressurized aerosol container, a propellant which consists of one or more of the conventionally-known aerosol propellants may be used to propel the compositions. A suitable propellant for use can be generally any liquifiable gas conventionally used for aerosol containers.

Suitable propellants for use are volatile hydrocarbon propellants which can include liquified lower hydrocarbons of 3 to 4 carbon atoms such as propane, butane and isobutane. Other suitable propellants are hydrofluorocarbons such as 1,2-difluoroethane (Hydrofluorocarbon 1 52A) supplied as Dymel 1 52A by DuPont. Other examples of propellants are dimethylether, N-butane, isobutane, propanes, nitrogen, carbon dioxide, nitrous oxide and atmospheric gas and mixtures thereof.

The aerosol propellant may be mixed with the present compositions and the amount of propellant to be mixed is governed by normal factors well known in the aerosol art. Generally, for liquifiable propellants, the level of propellant is from about 10% to about 60% by weight of the total composition, preferably from about 15% to about 40% by weight of the total composition.

Alternatively, pressurized aerosol dispensers can be used where the propellant is separated from contact with the hair spray composition such as a two compartment can of the type sold under the tradename SEPRO from American National Can Corp.

Other suitable aerosol dispensers are those characterized by the propellant being compressed air which can be filled into the dispenser by means of a pump or equivalent device prior to use. Such dispensers are described in U.S. Pat. No. 4,077,441, Mar. 7, 1978, Olofsson and U.S. Pat. No. 4,850,577, Jul. 25, 1989, TerStege, both incorporated by reference herein, and in U.S. Ser. No. 07/839,648, Gosselin et al., filed Feb. 21, 1992, also incorporated by reference herein. Compressed air aerosol containers suitable for use are also currently marketed by The Procter & Gamble Company under their tradename VIDAL SASSOON AIRSPRAY® hair sprays.

Conventional non-aerosol pump spray dispensers, i.e., atomizers, can also be used.

Other hair styling compositions include tonics and lotions, which are typically dispensed in a conventional bottle or tube, and applied directly to the hair or first dispensed to the hand and then to the hair.

The hair styling formulations of the present invention can optionally contain conventional hair care composition adjuvants. Generally, adjuvants collectively can comprise from about 0.05% to about 5% by weight and preferably from about 0.1% to about 3%, by weight. Such conventional optional adjuvants are well known to those skilled in the art and include in addition to those discussed above, emollients; lubricants and penetrants such as various lanolin compounds; protein hydrolysates and other protein derivatives; ethylene adducts and polyoxyethylene cholesterol; dyes, tints, bleaches, reducing agents and other colorants; pH adjusting agents sunscreens; preservatives; thickening agents (e.g. polymeric thickeners, such as xanthan gum); and perfume.

Method of Making

The hair styling compositions of the present invention can be made using conventional formulation and mixing techniques. It is critical to have the silicone grafted polymer completely dissolved in the ethanol as the first making step. Completely dissolved means no visible solids, solution is crystal clear. This can be done as a premix with ethanol so long as the polymer concentration in the premix does not exceed 15%. Alternatively, the polymer can simply be dissolved in the entire ethanol amount required for the batch. If ethanol is not to be used in the composition, a premix of the polymer with $C_3$ alkanol is prepared. Premixes with water are not feasible. The other ingredients can then be added with mixing to provide a homogeneous mixture. The neutralizer is preferably added to the premix prior to addition of other ingredients. A preferred order of addition is Isododecane. Isododecane is added prior to the addition of water, this is especially important for water levels above 15%.

Method of Use

The compositions of the present invention are used in conventional ways to provide the hair styling/holding benefits of the present invention. Such method generally involves application of an effective amount of the product to dry, slightly damp, or wet hair before and/or after the hair is arranged to a desired style. The composition is then dried or allowed to dry. By "effective amount" is meant an amount sufficient to provide the hair hold and style benefits desired considering the length and texture of the hair. In general, from about 0.5 g to about 50 g of product will be applied to the hair, depending upon the particular product formulation, dispenser type, length of hair, and type of hair style.

The following Experimentals and Examples further illustrate embodiments within the scope of the present invention. They are given solely for the purposes of illustration and are not to be construed as limitations of the present invention as many variations of the invention are possible without departing from its spirit and scope.

Experimentals

The following synthesis exemplify silicone grafted polymers useful in the present compositions.

Experimental 1: Batch synthesis

Place 20 parts acrylic acid, 60 parts t-butyl acrylate, and 20 parts polysiloxane (10,000 MW)-containing monomer in a flask. Add sufficient ethyl acetate or acetone as the reaction solvent to produce a final monomer concentration of 20%. Purge the vessel with an inert atmosphere, preferably nitrogen or argon. Add initiator, (2,2'-azobis-(2,4-dimethylvaleronitrile)) to a level appropriate for the desires molecular weight. Typically this is in the range of 0.5% to 1.0% by weight relative to the amount of monomer. Purge the vessel with an inert atmosphere, preferably nitrogen or argon. Heat to 60° C. and maintain this temperature for 8 hours while agitating. Terminate the reaction by cooling to room temperature. The polymer is purified by drying off the reaction solvent in an oven, or if acetone is used as the solvent precipitating the polymer, by adding water and then drying the precipitate.

Experimental 2: Semi-continuous synthesis

Place 20 parts acrylic acid, 60 parts t-butyl acrylate, and 30 parts polysiloxane (10,000 MW)-containing monomer in a flask. Add sufficient ethyl acetate or acetone as the reaction solvent to produce a final monomer concentration of 25%. Purge the vessel with an inert atmosphere, e.g. nitrogen or argon. Add initiator, (2,2'-azobis-(2,4-dimethylvaleronitrile)) as in Experimental 1. Heat to 60° C. and maintain this temperature. After polymerization of these monomers has proceeded about 15 minutes to about 1 hour, e.g. about 30 minutes, add a second monomer charge of 20 parts acrylic acid and 60 parts t-butyl acrylate, to give a final total monomer charge of approximately 40% by weight. Maintain at temperature for 8 hours. Terminate the reaction and purify the polymer as in Experimental 1.

EXAMPLES

Examples 1–8

The following examples represent nonaerosol hairspray compositions of the present invention.

| Component (wt. %) | Example No | | | | | | | |
|---|---|---|---|---|---|---|---|---|
| | 1 | 2 | 3 | 4 | 5 | 6 | 7 | 8 |
| Non-Silicone Polymer[1] | 1.00 | 1.25 | 1.50 | 1.00 | 3.50 | 1.70 | 4.50 | 2.0 |
| Silicone Grafted Polymer[2] | 3.00 | 3.75 | 4.50 | 4.50 | 2.50 | 4.80 | 0.50 | 2.0 |
| Isododecane[3] | 1.00 | 1.00 | 1.00 | 3.00 | 0.50 | 1.0 | 2.00 | 0.02 |
| Diisopropyl butyl adipate | 0.40 | 0.75 | 0.90 | 0.55 | 1.52 | 1.30 | 0.75 | 0.40 |
| Sodium hydroxide[4] | 0.96 | 1.20 | 1.44 | 1.6 | — | 1.69 | — | 1.11 |
| Potassium hydroxide[5] | — | — | — | — | 1.35 | — | 0.44 | — |
| Perfume | 0.10 | 0.10 | 0.10 | 0.10 | 0.10 | 0.15 | 0.10 | 0.15 |
| Water | 17.00 | 20.00 | 20.00 | 18.00 | 11.05 | 20.00 | 13.71 | 39.24 |
| Sodium Benzoate | — | — | — | — | — | 0.10 | — | 0.10 |
| Ethanol[6] | 76.54 | 71.95 | 70.56 | 71.25 | 79.5 | 69.26 | 78.00 | 54.98 |

[1]75% t-butyl acrylate/25% acrylic acid, having a weight average molecular weight of about 80,000.
[2]60% t-butyl acrylate/20% acrylic acid/20% silicone macromer (weight average molecular weight of silicone macromer of about 10,000), having a weight average molecular weight of about 130,000.
[3]PERMETHYL 99A, from Presperse, Inc., South Plainfield, NJ, USA.
[4]Sodium hydroxide is 30% active.
[5]Potassium hydroxide is 45% active.
[6]SDA 40 (100% ethanol).

Examples 9–14

The following examples represent aerosol hairspray compositions of the present invention.

| Component (wt. %) | Example No. | | | | | |
|---|---|---|---|---|---|---|
| | 9 | 10 | 11 | 12 | 13 | 14 |
| Non-Silicone Polymer[1] | 1.25 | 1.13 | 1.0 | 3.75 | 2.62 | 1.00 |
| Silicone Grafted Polymer[2] | 3.75 | 3.38 | 2.50 | 1.25 | 0.88 | 2.50 |
| Isododecane[3] | 0.50 | 0.50 | 2.00 | 1.00 | 0.25 | 0.50 |
| Triethyl citrate[4] | — | — | 0.21 | — | — | — |
| Diisopropyl butyl adipate | 0.50 | 0.45 | — | 0.75 | 0.53 | 0.35 |
| Propylene glycol | — | — | 0.02 | — | — | — |
| Sodium hydroxide[5] | 1.11 | 0.94 | — | — | 0.78 | — |
| Potassium hydroxide[6] | — | — | 0.33 | 1.04 | — | 0.73 |
| Perfume | 0.10 | 0.10 | 0.10 | 0.10 | 0.10 | 0.10 |
| Water | 16.00 | 16.00 | 7.00 | 15.00 | 39.94 | 8.00 |
| Sodium Benzoate | 0.10 | 0.10 | — | 0.10 | 0.20 | — |
| Ethanol[7] | 56.69 | 57.42 | 62.85 | 52.99 | 29.75 | 54.5 |
| Propellant - Isobutane | — | — | 7.02 | 15.00 | 10.00 | — |
| Propellant - n-butane | 10.00 | 10.00 | — | — | — | — |
| Propellant - Dimethyl ether[8] | 10.00 | 10.00 | — | 15.00 | 15.00 | — |
| Propellant - Hydrofluorocarbon 152a[9] | — | — | 15.98 | — | — | 32.32 |

[1]75% t-butyl acrylate/25% acrylic acid, having a weight average molecular weight of about 80,000.
[2]60% t-butyl acrylate/20% acrylic acid/20% silicone macromer (weight average molecular weight of silicone macromer of about 10,000), having a weight average molecular weight of about 150,000.
[3]PERMETHYL 99A, from Presperse, Inc., South Plainfield, NJ, USA.
[4]CITROFLEX-2, from Morflex, Inc., Greensboro, NC, USA.
[5]Sodium hydroxide is 30% active.
[6]Potassium hydroxide is 45% active.
[7]SDA 40 (100% ethanol).
[8]DYMEL - A, from Dupont.
[9]DYMEL-152a, from Dupont.

In Examples 1–10, the compositions are prepared as described above, by first mixing the polymer with the ethanol, neutralizing the polymer with sodium or potassium hydroxide, then adding sequentially (as, applicable) with mixing, isododecane, plasticizer, perfume, and water. If sodium benzoate is used, it is added after water addition. Most preferably a premix of water and sodium benzoate is made and then added after the main water addition. Propellants for aerosol compositions are charged to conventional aerosol containers after the remainder of the prepared composition has been added.

What is claimed is:

1. A hair styling composition comprising:
   (a) from about 0.1% to about 15%, by weight, of a non-silicone adhesive polymer having a weight average molecular weight of greater than about 20,000, said polymer being characterized by an organic polymeric backbone wherein said polymer is substantially free of silicone, and wherein said polymer comprises monomers selected from the group consisting of: acrylamide monomers, acrylate monomers, methacrylate monomers, and combinations thereof;
   (b) from about 0.1% to about 15%, by weight, of a silicone grafted adhesive polymer, said polymer being characterized by an organic polymeric backbone, compatible with said adhesive polymer of (a) wherein said silicone grafted adhesive polymer has silicone macromers grafted to said backbone and wherein the number average molecular weight of said silicone macromers is greater than about 500;
   (c) from about 0.1% to about 15%, by weight, of a hydrocarbon solvent selected from the group consisting of $C_{10}$–$C_{14}$ branched chain hydrocarbons, and mixtures thereof having a boiling point of from about 105° C. to about 260° C.; and
   (d) a polar solvent phase comprising from about 80% to about 99%, by weight of the composition, of a polar solvent selected from the group consisting of water and $C_2$–$C_3$ monohydric alcohols, and mixtures thereof, wherein said composition contains no more than about 15%, by weight, of $C_3$ monohydric alcohol;

wherein said organic polymer backbones of (a) and (b) are soluble in said polar solvent phase, and said silicone macromers of said silicone grafted adhesive polymer are soluble in said hydrocarbon solvent.

2. A hair styling composition as in claim 1, wherein said composition comprises:
   (a) from about 0.5% to about 8%, by weight, of said non-silicone adhesive polymer having a weight average molecular weight of greater than about 30,000;
   (b) from about 0.5% to about 8%, by weight, of said silicone grafted polymer;
   (c) from about 0.5% to about 10%, by weight, of said hydrocarbon solvent;
   (d) from about 85% to about 98%, by weight, of said polar solvent, wherein said composition contains no more than about 12%, by weight, of $C_3$ monohydric alcohol.

3. A hair styling composition as in claim 1, wherein said composition comprises:
   (a) from about 1% to about 8%, by weight, of said non-silicone adhesive polymer;
   (b) from about 1% to about 8%, by weight, of said silicone grafted polymer;
   (c) from about 2% to about 8%, by weight, of said hydrocarbon solvent;
   (d) from about 80% to about 99%, by weight, of said polar solvent, wherein said composition contains no more than about 12%, by weight, of $C_3$ monohydric alcohol and said composition contains at least about 10%, by weight, of water and no more than 80%, by weight, of volatile organic compounds.

4. A hair styling composition as in claim 1, wherein said composition comprises no more than 80% of volatile organic compounds.

5. A hair styling composition as in claim 1, wherein said silicone grafted polymer comprises from about 50% to about 99%, by weight, of non-silicone macromer-containing monomer units and from about 1% to about 50%, by weight of silicone macromer-containing monomer units.

6. A hair styling composition as in claim 1, wherein said silicone grafted polymer comprises from about 60% to about 98%, by weight, of non-silicone macromer-containing monomer units and from about 2% to about 40%, by weight of silicone macromer-containing monomer units.

7. A hair styling composition as in claim 5, wherein said silicone grafted polymer comprises from about 1% to about 99%, by weight, of hydrophilic monomer units and from about 0% to about 99%, by weight, of hydrophobic monomer units.

8. A hair styling composition as in claim 6, wherein said silicone grafted polymer comprises from about 5% to about 80%, by weight, of hydrophilic monomer units and from about 1% to about 90%, by weight, of hydrophobic monomer units.

9. A hair styling composition as in claim 5, wherein said silicone grafted polymer comprises from about 10% to about 50%, by weight, of hydrophilic monomer units and from about 5% to about 85%, by weight, of hydrophobic monomer units.

10. A hair styling composition as in claim 9, wherein said silicone grafted polymer comprises from about 15% to about 40%, by weight, of hydrophilic monomer units and from about 15% to about 80%, by weight, of hydrophobic monomer units.

11. A hair styling composition as in claim 7, wherein said hydrophilic monomer units are selected from the group consisting of acrylic acid, methacrylic acid, N,N-dimethylacrylamide, dimethyl aminoethyl methacrylate, quaternized dimethylaminoethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, diallyidimethyl ammonium chloride, vinyl pyrrolidone, vinyl ethers, maleimides, vinyl pyridine, vinyl imidazole, styrene sulfonate, allyl alcohol, vinyl alcohol, and salts of acids and amines above, and mixtures thereof.

12. A hair styling composition as in claim 11, wherein said hydrophilic monomer units are selected from the group consisting of acrylic acid, N,N-dimethyl acrylamide, dimethylaminoethyl methacrylate, quaternized dimethyl aminoethyl methacrylate, vinyl pyrrolidone, salts of acids and amines thereof, and mixtures thereof.

13. A hair styling composition as in claim 11, wherein said hydrophobic monomer units are selected from the group consisting of acrylic and methacrylic acid esters of $C_1$–$C_{18}$ alcohols, styrene; polystyrene macromer; vinyl acetate; vinyl chloride; vinylidene chloride; vinyl propionate; alpha-methylstyrene; t-butylstyrene; butadiene; cyclohexadiene; ethylene; propylene; vinyl toluene; and mixtures thereof.

14. A hair styling composition as in claim 1, wherein said hydrocarbon solvent is selected from the group consisting of saturated $C_{10}$–$C_{14}$ branched chain hydrocarbons, and mixtures thereof.

15. A hair styling composition as in claim 2, wherein said hydrocarbon solvent is selected from the group consisting of $C_{11}$–$C_{13}$ branched chain hydrocarbons.

16. A hair styling composition as in claim 15, wherein said hydrocarbon solvent is isododecane.

17. A hair styling composition as in claim 1, wherein said hydrocarbon solvent is a $C_{11}$–$C_{13}$ branched chain hydrocarbon.

18. A hair spray composition comprising a composition as in claim 1 disposed within a hair spray dispenser.

19. A hair spray composition comprising:
   (a) from about 1% to about 8%, by weight, of a non-silicone adhesive polymer having a weight average molecular weight of greater than about 20,000, said polymer being characterized by an organic polymeric backbone wherein said polymer is substantially free of silicone, and wherein said polymer comprises monomers selected from the group consisting of acrylamide monomers, acrylate monomers, methacrylate monomers, and combinations thereof;
   (b) from about 1% to about 8%, by weight, of a silicone grafted adhesive polymer, said polymer being characterized by an organic polymeric backbone, compatible with said adhesive polymer of (a) wherein said silicone grafted adhesive polymer has silicone macromers grafted to said backbone and wherein the number average molecular weight of said silicone macromers is greater than about 500;
   (c) from about 0.1% to about 15%, by weight, of a hydrocarbon solvent selected from the group consisting of $C_{101}$–$C_{14}$ branched chain hydrocarbons, and mixtures thereof having a boiling point of from about 105° C. to about 260° C.; and
   (d) a polar solvent phase comprising from about 80% to about 99%, by weight the composition, of a polar solvent selected from the group consisting of water and $C_2$–$C_3$ monohydric alcohols, and mixtures thereof, wherein said composition contains no more than about 15%, by weight, of $C_3$ monohydric alcohol and from about 10% to about 50%, by weight of the composition, of water;

wherein said organic polymer backbones of (a) and (b) are formed of the same monomers and are soluble in said polar solvent phase, and said silicone macromers of said silicone grafted adhesive polymer are soluble in said hydrocarbon solvent.

20. A hair spray composition as in claim 19, wherein the weight ratio of (a) to (b) is from 1:4.5 to 9:1.

* * * * *